United States Patent [19]

Sunshine et al.

[11] Patent Number: 4,868,214
[45] Date of Patent: Sep. 19, 1989

[54] ONSET-HASTENED/ENHANCED ANALGESIA

[75] Inventors: Abraham Sunshine, New York; Eugene M. Laska, Larchmont, both of N.Y.

[73] Assignee: Analgesic Associates, Larchmont, N.Y.

[21] Appl. No.: 121,849

[22] Filed: Nov. 17, 1987

[51] Int. Cl.⁴ .............................................. A61K 31/19
[52] U.S. Cl. ................................... 514/568; 514/570; 514/557; 514/947; 514/960; 514/962
[58] Field of Search ............... 514/557, 568, 570, 947, 514/960, 962

[56] References Cited

U.S. PATENT DOCUMENTS 4,533,546 8/1985 Kishi et al. .......................... 514/570
4,534,980 8/1985 Itoh et al. ............................ 514/570

Primary Examiner—Jacqueline V. Howard
Attorney, Agent, or Firm—Burns, Doane, Swecker & Mathis

[57] ABSTRACT

Onset-hastened and enhanced analgesic response is elicited in a mammalian organism in need of such treatment, i.e., a mammal suffering pain, by administering thereto a unit dosage onset-hastening/enhancing analgesically effective amount of the S(+) ketoprofen enantiomer, said enantiomer being substantially free of its R(−) ketoprofen antipode.

41 Claims, No Drawings

ONSET-HASTENED/ENHANCED ANALGESIA

CROSS-REFERENCE TO COMPANION APPLICATIONS

Our copending applications, Serial No. 071,914, filed July 10, 1987, and Serial No. 121,848, filed concurrently herewith, both assigned to the assignee hereof.

BACKGROUND OF THE INVENTION

1. Field of the Invention

The present invention relates to the use of S(+) ketoprofen to elicit an onset-hastened and enhanced analgesic response in mammalian organisms in need of such treatment, and to certain pharmaceutical compositions comprising unit dosage effective amounts of S(+) ketoprofen.

2. Description of the Art

Ketoprofen, also known as DL-2-(3-benzoylphenyl)-propionic acid, has the structural formula The compound is well-known as a nonsteroidal anti-inflammatory drug having analgesic and antipyretic activity. In the United States, ketoprofen is marketed under the tradename Orudis ®. Other tradenames or codenames include RP 19583, Alrheumat, Alrheumun, Capisten, Fastum, Iso-K, Kefenid, Ketopron, Lertus, Meprofen, Oruvail and Profenid. As Orudis ®, the drug is avadilable by prescription in the U.S. as capsules containing 25 mg, 50 mg dor 75 mg of ketoprofen, indicated for the acute or long-term treatment of the signs and symptoms of rheumatoid arthritis or osteoarthritis. Orudis ® is recommended at a daily dose of 150 to 300 mg, divided in three or four doses. It is recommended that drug treatment begin at 75 mg three times or 50 mg four times a day. Small people may need smaller doses. Daily dosages should not exceed 300 mg per day. See also *Physician's Desk Reference*, 41st edition, 1987, publisher Edward R. Barnhart, Medical Economics Company, Inc., Oradell, NJ 07649, pp. 2179–2181. For mild to moderate pain and dysmenorrhea, a dose of 25 mg to 50 mg every 6 to 8 hours as needed was recently approved by the Food and Drug Administration ("F.D.A.").

As is apparent from its chemical nomenclature, ketoprofen is a racemic mixture. It is only the racemic mixture which has in fact ever been marketed. There have, however, been a few studies of the individual S(+) and R(−) isomers reported in the literature. These reflect that there is significant conversion of the R(−) isomer to the S(+) enantiomer, the latter being presumed by analogy with other 2-arylpropionic acids to be the active form of ketoprofen.

Hutt et al, *J. Pharm. Pharmacol.*, 35, 693–704 (1983), reviewed the earlier work on the metabolic chiral inversion of 2-arylpropionic acids, including ibuprofen, which they indicate was the first substituted 2-arylpropionic acid conclusively shown to undergo the inversion as well as the most studied member of the group. The authors noted that early workers found no significant difference in in vivo activity among the R(−) and S(+) isomers and the racemic mixture of ibuprofen in three different animal models, but very large differences in vitro between the R(−) and S(+) isomers, ascribing this discrepancy to the virtually quantitative conversion of the R(−) to the active S(+) isomer in vivo. Hutt et al indicated similar properties for fenoprofen; the enantiomers of fenoprofen were reported to be of equal potency in animal test systems. No animal test information for the enantiomers of ketoprofen were reported. However, it was noted that ketoprofen, like fenoprofen, was known to undergo incorporation into triglycerides, an indirect indication of chiral inversion. Other indirect evidence was also discussed.

In the same paper, Hutt et al reported that, in contrast, for several other 2-arylpropionic acids, the inactive R(−) isomer was not converted in vivo to the active S(+) isomer as readily as ibuprofen and fenoprofen, although the conversion seemed to occur to some extent over time. Naproxen, they noted, has been the only compound marketed as the S(+) enantiomer to date. And in the case of indoprofen, the R(−) enantiomer was found to be about 20 times less pharmacologically active in rats and mice in vivo than the S(+) isomer. Hutt et al concluded:

It is likely that benefits will be obtained from the use of the S(+)-enantiomer of 2-arylpropionates as drugs as opposed to the racemates. This is only found at present in the case of naproxen. In cases of rapid inversion, the inactive R(−) isomer serves merely as a prodrug for the active S(+)-antipode. Where inversion is slow, the R(−) enantiomer is an unnecessary impurity in the active S(+) form. Use of the S(+)-enantiomer would permit reduction of the dose given, remove variability in rate and extent of inversion as a source of variability in therapeutic response and would reduce any toxicity arising from nonstereospecific mechanisms.

Thus, in cases of rapid inversion, such as ibuprofen and fenoprofen, where substantially equivalent in vivo responses have been reported for the individual enantiomers and the racemic drug, Hutt et al suggested that no benefits would be obtained from the use of the S(+) isomer because the inactive R(−) isomer merely acts as a prodrug for the active S(+) form. Contrariwise, in cases where chiral inversion is slow, e.g. naproxen and indoprofen, the use of the S(+) enantiomer is desirable for several reasons enumerated by Hutt et al. Indeed, naproxen has been reported to be marketed as the d-isomer for one of the reasons given by Hutt et al, i.e. to reduce side effects (Allison et al, "Naproxen," Chapter 9 in *Anti-inflammatory and Anti-Rheumatic Drugs*, eds. Rainsford and Path, CRC Press Inc., Boca Raton, Florida, 1985, p. 172).

Another general report on earlier work has been provided by Hutt et al in *Clinical Pharmacokinetics*, 9, 371–373 (1984). In this article on the importance of stereochemical considerations in the clinical pharmacokinetics of 2-arylpropionic acids, the authors tabulated relative potencies of the enantiomers of a number of 2-arylpropionic acidsin vivo and in vitro. The in vitro results showed the S or (+) isomer in each case to be the active species. In vivo, however, the results were not consistent across the entire class. Thus, the results for naproxen and indoprofen demonstrate the S or (+) isomer to be much more active in vivo, indicating a relatively slow inversion of the inactive R or (−) isomer to the active S or (+) isomer; the results for fenoprofen and ibuprofen, on the other hand, demonstrate the inactive R or (−) and the active S or (+) isomers tobe approximately equally effective in vivo, indicating a rapid inversion of R or (−) isomer to S or (+) isomer. The reference is silent, however, as to the activity of the enantiomers of ketoprofen.

Rendic et al, *Il. Farmaco-Ed. Sci.* 35(1), 51–59 (1980) investigated the binding properties of the + and − enantiomers of ketoprofen to human serum albumin (HSA). The authors indicated that their research was prompted by recent reports of the pharmacokinetic and therapeutic effects of racemic ketoprofen in humans, together with the generally accepted view that S-enantiomers of chiral derivatives of α-phenylpropionic acids have predominant, if not exclusive, anti-inflammatory activity. They found stereoselectivity in binding to HSA, especially at lower concentrations of ligands and of protein.

Lombard et al, *IRCS Med. Sci.* 13(10), 1025 (1985), found appreciable enrichment of S(+) ketoprofen in rat total liver homogenate after incubation with the racemic compound. Enrichment was already notable after 2 hours and no S(+) to R(−) conversion was found. The authors attributed the significant conversion of R(−) to S(+) in the liver to microsomal enzymes. In related research, Rossetti et al, *IRCS Med. Sci.* 14(3), 256-257 (1986), found that administration of racemic ketoprofen to rats gave significant enrichment of the S(+) isomer in urine.

The disposition of the enantiomers of racemic ketoprofen in normal rabbits as well as in rabbits with diminished renal function was studied by Abas et al, *Clin. Exp. Pharmacol. Physiol, Suppl.* 9, 41-42 (1985). Since acyl glucuronide formation accounts for most ketoprofen elimination in rabbits and man, the authors investigated whether intravenous administration of racemic ketoprofen leads to R to S inversion and whether the proportion of active S isomer in plasma would increase with renal dysfunction. Abas et al found that, in normal rats, 76% of R was inverted to S, assuming that unrecovered and recovered doses had the same enantiomeric composition. The authors stated: "The plasma AUC of the racemic compound was not increased in animals with i.v. uranyl induced renal failure (RF). This may be due to the high fraction of this enantiomer cleared by inversion rather than acyl glucuronide formation. (Congress abstract)." Thus, results in rabbits with impaired renal function were unclear.

Abas et al most recently reported on their studies of ketoprofen dispostion in normal and renally impaired rabbits in *J. Pharmacol. Exp. Ther.*, 240(2), 637-641 (1987). The authors noted that ketoprofen is a racemate and like other 2-arylpropionic acid NSAID's, would be expected to undergo chiral inversion of the R to the S enantiomer, but that no data had been pulbished on the question. Indeed, their work reported in *J. Pharmacol. Exp. Ther.* appears to be the only instance in which the separate enantiomers of ketoprofen were separately administered in vivo.

In their work reported in *J. Pharmacol. Exp. Ther.*, Abas et al showed enantiospecific inversion of R(−) to S(+) ketoprofen. However, the authors determined that only 9% of the R(−) enantiomer of ketoprofen was inverted to S, compared with 70% for its close structural analog, R(−) fenoprofen. [Hayball et al, *J. Pharmacol. Exp. Ther.* 240(2), 631-636 (1987)]. Blood samples were collected before and at 0.08, 0.25, 0.5, 0.75 and 1.0 hour, then hourly until 8 hours after dosing. While Abas et al did not discuss any differences in amounts of inversion at the early time points, it might appear from their FIG. 2a that very substantial inversion of R to S occurred in the first hour after dosing, although the overall amount of conversion over time is not nearly as large.

Abas et al noted that their bound plus unbound ketoprofen concentration data had its limitations. The absence of plasma protein binding data for the individual enantiomers in rabbits meant it was impossible to calculate dispositional parameters for unbound drug; the authors were unable to examine selective clearance and distribution of the enantiomers independent of enantioselective effects on plasma protein binding. It would have been desirable to measure unbound ketoprofen; unfortunately, the assay methodology was not of sufficient sensitivity to allow such measurements.

Abas et al indicated that the implications of their findings were uncertain, given the complexities of competing clearance processes, and relevance to humans may depend on a variety of factors. See also Meffin et al, *J. Pharmacol. Exp. Ther.* 238, 280-287 (1986).

In summary, the current state of the art assumes that, in mammals, by analogy to another 2-arylpropionic acid NSAID's, the S(+) form is the active enantiomer of ketoprofen. The art recognizes that there is a significant conversion in vivo of R(−) to S(+), with no noted conversion of S(+) to R(−). However, there do not appear to be any animal experiments on efficacy of the separate enantiomers reported in the literature. The prior art, moreover, is conspicuously silent in respect to any onset-hastened/enhanced alleviation of mammalian pain utilizing whatever form of the ketoprofen drug species.

SUMMARY OF THE INVENTION

Surprisingly, the present inventors now find that S(+) ketoprofen can be advantageously administered to mammals suffering from pain, especially humans, to not only elicit a more potent analgesic response but also to evoke such response more rapidly than possible by administration of the same dose of ketoprofen in its racemic form.

This is particularly surprising in light of the art's failure toeven investigate the activity in vivo for S(+) ketoprofen versus the R(−) isomer and the racemic mixture, far less the art's failure to make telling observations of the pain level or amount of relief at meaningful time points sufficiently soon after dosing in an appropriate analgesic model.

In one aspect, the present invention thus provides a method of hastening the onset of analgesia in a mammal, said method comprising administering to a mammal in need of such treatment an effective onset-hastening analgesic amount of S(+) ketoprofen substantially free of R(−) ketoprofen.

In another aspect, the present invention provides a method of eliciting an enhanced analogesic response in a mammal, particularly shortly after dosing, said method comprising administering to a mammal in need of such treatment an effective analgesia denhancing amount of S(+) ketoprofen substantially free of R(−) ketoprofen.

In yet another aspect, the present invention provides a pharmaceutical composition of matter for use in eliciting an onset hastened and enhanced analgesic response in mammals, especially humans, said composition comprising an effective analgesic unit dosage amount of S(+) ketoprofen substantially free of R(−) ketoprofen. Typically, S(+) ketoprofen is associated with a nontoxic pharmaceutically acceptable inert carrier or diluent therefor.

DETAILED DESCRIPTION OF THE PREFERRED EMBODIMENTS OF THE INVENTION

The term "ketoprofen" or "racemic ketoprofen" as used herein is intended to encompass not only DL-2-(3-benzoylphenyl)propionic acid itself but also any pharmaceutically acceptable salt thereof.

The term "S(+) ketoprofen" as used herein is intended to encompass not only the dextrorotatory or S(+) isomer of 2-(3-benzoylphenyl)propionic acid but also any pharmaceutically acceptable, analgesically effective salt thereof. The expression "substantially free of R(−) ketoprofen" as used in conjunction with the term "S(+) ketoprofen" means that the S(+) ketoprofen is sufficiently free of R(−) ketoprofen [which is the levorotatory form or R(−) isomer of 2-(3-benzoylphenyl)-propionic acid or salt thereof] to exert the desired onset-hastened and enhanced analgesic effect. Practically speaking, this means that the active ingredient should contain at least 90% by weight S(+) ketoprofen and 10% or less by weight R(−) ketoprofen. Preferably, the weight ratio of S(+) ketoprofen to R(−) ketoprofen is greater than or equal to 20:1, more preferably greater than 97:3. Ideally the S(+) ketoprofen is 99 or more % by weight free of R(−) ketoprofen, i.e., the weight ratio of S or R is approximately equal to or greater than 99:1. At the present time, a 20:1 ratio of S(+) to R(−) is readily obtainable from racemic ketoprofen by literature methods and eminently useful in the practice of the present invention.

Where specific amounts of S(+) ketoprofen are set forth below, it should be understood that, unless otherwise specified, the amounts are given in mg of the acid, not of a salt. Moreover, unless otherwise specified, for simplicity's sake the amounts given represent total ketoprofen content, most of which is in the S(+) form. For example, "50 mg S(+) ketoprofen" means 50 mg total ketoprofen at least 90% of which is in the S(+) form, preferably at least 95%.

S(+) ketoprofen, in accord with the present invention, produces the following unexpected results:

(1) the analgesic effect of ketoprofen on the mammal is brought on more quickly than by use of the same dose of racemic ketoprofen; and (2) a greater analgesic response is elicited in the early hours than is elicited by the same dose of racemic ketoprofen.

These unexpected results can be achieved in the treatment of pain responsive to an NSAID (non-steroidal antiinflammatory drug) and specifically pain associated with inflammation. This includes postpartum and postoperative pain, dental pain, headache pain, dysmenorrhea, pain of musculoskeletal origin and pain and discomfort associated with respiratory infections such as colds and flu.

For patients suffering from such pain, who require treatment at a particular dose of racemic ketoprofen, the time from administration of medication to the onset of effective relief is clearly of paramount importance. The present inventors' discovery that S(+) ketoprofen, when used in place of racemic ketoprofen at the same dose, substantially shortens the onset time (i.e., substantially hastens the onset) of analgesia is therefore very significant. It is likewise quite unexpected. Moreover, in patients suffering from inflammatory or degenerative joint disease, e.g. rheumatoid arthritis, osteoarthritis, gout or acute musculo-skeletal disease, the substantial shortening of analgesic onset is extremely important; pain is an important component of these disease states and more rapid relief from pain is of substantial psychological benefit. The S(+) ketoprofen will, of course, over time provide relief from other aspects of inflammatory disease as well, including, e.g. morning stiffness.

In a group responsive to a given dose of the racemate, it is believed that onset time for analgesia can be reached, on the average, about one-third sooner when S(+) ketoprofen is used rather than when racemic ketoprofen is administered, depending on the dose level and the severity of the pain, but particularly at the low end (12.5–50 mg) of the analgesic dosage range and for patients with moderate pain.

Insofar as concerns enhanced analgesia, more pronounced analgesia is obtained when S(+) ketoprofen is used at the same dose level as racemic keotprofen, especially during the first few hours.

The precise amount of S(+) ketoprofen for use in accord with the present invention will vary depending, for example, on the size and kind of the mammal and the condition for which the drug is administered. For use in humans, the analgesically effective amount of S(+) ketoprofen will typically be from about 12.5 to 75 mg, although greater amounts (e.g. 100 mg) may be employed if needed for pain relief and if tolerated by the patient. The daily dose in humans preferably will not exceed 300 mg S(+) ketoprofen, although greater amounts could be employed if tolerated by the patient. Preferred unit dosage compositions for use in the treatment of mild to moderate pain having an inflammatory component contain 12.5, 25, 50 or 75 mg S(+) ketoprofen.

While the compositions for use in the invention are preferably for oral use, they may also be formulated for and administered by other routes which are known for administering non-narcotic analgesics/nonsteroidal antiinflammatory drugs, e.g. as suppositories or parenteral solutions, or as topical formulations such as ointments, gels, creams, lotions solutions, impregnated bandages or other topical delivery devices, and so forth. Also, it should be noted that the preferred human dosage levels indicated above are for use in adults; pediatric compositions would contain proportionately less of the active ingredient.

The compositions for use herein are very conveniently administered to mammals by any route of administration suitable for racemic ketoprofen, e.g. oral, rectal, topical or parenteral. Preferably S(+) ketoprofen is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, Pa. 18042. In a typical preparation for oral administration, e.g. tablet, capsule or caplet, S(+) ketoprofen in an effective analgesic amount and substantially free of R(−) ketoprofen, is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulosic, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar. Such compositions should preferably contain at least 0.1% of S(+) ketoprofen; generally, S(+) ketoprofen will be from about 2% to about 60% of the weight of the unit. Typical unit dosage forms for oral administration will contain about 12.5 to 75 mg, preferably 25 to 50 mg, S(+) ketoprofen, if formulated for immediate release, as is preferred. If the composition is intended for sustained release, much larger amounts of the active ingredient would of course be incorporated into an individual unit; in such case, at least 12.5, and preferably up to 50 or 75 mg of the total amount of S(+) ketoprofen, should be formulated for immediate release so as to obtain the desired degree of enhanced analgesia and hastened onset A typical capsule for oral administration may contain, in addition to the selected amount of S(+) ketoprofen, the following combination of inactive ingredients/carrier materials: D&C Yellow 10, FD&C Blue 1, FD&C Yellow 6, gelatin, lactose, magnesium stearate and titanium dioxide.

Moreover, the compositions for use in obtaining enhanced analgesia and hastened onset in accord with the present invention may, in addition to the selected dose of S(+) ketoprofen, also contain other active ingredients and/or enhancing agents. Thus, for example, S(+) ketoprofen may be combined with such ingredients and agents as have been described for combination with racemic ketoprofen, e.g. caffeine or other xanthine derivative, a narcotic analgesic (with or without caffeine), a skeletal muscle relaxant, an antihistamine, decongestant, cough suppressant and/or expectorant. See, for example, Sunshine et al U.S. Pat. No. 4,486,436, issued Dec. 4, 1984; Sunshine et al U.S. Pat. No. 4,552,899, issued Nov. 12, 1985; Sunshine et al U.S. Pat. No. 4,567,183, issued Jan. 28, 1986; and Sunshine et al U.S. Pat. No. 4,619,934, issued Oct. 28, 1986; and Sunshine et al pending U.S. Pat. Application Ser. No. 815,502, filed Jan. 2, 1986.

The enhanced analgesic effect and hastened onset obtained by use of S(+) ketoprofen in comparison with racemic ketoprofen can be evaluated in animal and human studies such as those described below.

ANTIPHENYLQUINONE WRITHING TEST

This test is a standard procedure for detecting and comparing analgesic activity and generally correlates well with human efficacy.

Mice are first dose with the medications studied. The medications used are two dose levels of S(+) ketoprofen and two dose levels of racemic ketoprofen. The mice are then challenged with phenyl-p-benzoquinone given intraperitoneally and observed for the characteristic stretch-writhing syndrome. Lack of wirthing constitutes a positive response. The degree of analgesic protection can be calculated on the basis of suppression of writhing relative to control animals run the same day. Time response data are also obtained. Observations are made early enough post-dosing to detect differences in onset. The test is a modification from the methods of Sigmund et al and Blumberg et al (Sigmund, E., Cadmus, R., and Lu, G., *Proc. Soc. Exp. Biol.* and *Med.* 95, 729–731, 1957; Blumberg, H., et al, *Proc. Soc. Exp. Biol. and Med.* 118, 763–766, 1965).

THE INFLAMED RAT PAW TEST: PRESSURE INDUCED STIMULI

The method of Randall-Selitto, modified according to Winter et al, is used to ascertain the escape response threshold resulting from the application of increasing pressure to the yeast inflamed left hind paw. Drug treatment is given. The medications studied are two dose levels of S(+) ketoprofen and two dose levels of racemic ketoprofen. A constantly increasing force is applied to the paw and the "flight reaction" is observed and recorded at several points in time (Randall, L. Q., and Selitto, J. J.: *Arch. Int. Pharmacodyn.*, II, 409–419, 1957; Winter, C. A., and Lars, F.: *J. Pharmacol. Exp. Therap.* 148, 373–379, 1965). Observations are made early enough post-dosing to detect differences in onset.

To establish the efficacy of the compositions of this invention in humans, patients with moderate to severe pain requiring an oral analgesic/anti-inflammatory agent, can be administered S(+) ketoprofen or racemic ketoprofen. Typical pain models include dysmenorrhea, post-operative pain, post-partum pain and dental extraction pain. Either a crossover design or a completely randomized design can be used. To determine analgesic efficacy, an observer interviews the patients as to their level of pain at subsequent periods of time. Patients are asked to subjectively estimate the time at which the medication begins to provide significant relief. Patients may be given a stopwatch to help estimate onset more accurately. Appropriate statistical methods, including survival analysis, can be used to show that the S(+) enantiomer has shorter onset and is more efficacious (Laska, E., Gormely, M., Sunshine, A., Belleville, J. W., Kantor, T., Forreset, W. H., Siegel, C. and Meisner, M., "A Bioassay Computer Program for Analgesic Clinical Trials," *Clin. Pharmacol. Ther.* 8: 658, 1967; Cox, D. R., "Regression Models and Life Tables," *Journal Royal Statistical Society,* Series B, Volume 34: 187–202, 1972).

S(+) ketoprofen for use in the method and compositions of the present invention can be prepared by a variety of methods, such as by resolution of racemic ketoprofen.

Farge et al U.S. Pat. No. 3,641,127 describes the preparation of racemic ketoprofen and related compounds; see, in particular, Example V thereof. The Farge et al patent also describes, a method for preparing the individual D- and L-isomers by oxidation of the corresponding optically active (3-benzylphenyl)alkanoic acids; see column 3, lines 22–40.

Abas et al., *J. Pharmacol. Exp. Ther.* 240(2), 637–641 (1987), have resolved racemic ketoprofen using a modification of the method of Blazevic et al, *Acta Pharmacol.*

*Jugoslav.* 25, 155–164 (1975). Abas et al prepared the diastereoisomeric amides of R(−) and S(+) ketoprofen with (+)-R-1-methylbenzylamide from racemic ketoprofen, via the acid chlorides using thionyl chloride. The diastereoisomeric amides were separated by the HPLC (high performance liquid chromatographic) method of Sallustio et al, *Journal of Chromatography* 374, 329–337 (1986), but using a 7.8 mm×300 mm preparative column. The pure amides were then separately converted to nitroso derivatives with dinitrogen tetroxide, and the nitroso derivatives were thermally decomposed to the respective ketoprofen enantiomers as described by Balzevic et al. Purification of the R and S enantiomers by silica gel chromatography, recrystallization from diethyl ether/cyclohexane and HPLC analysis according to Sallustio et al's method afforded the R and S enantiomers with enantiomeric purities o 98% and 95%, respectively.

HPLC methods other than Sallustio et al's for resolving enantiomers of NSAID's such as ibuprofen and fenoprofen, and likely adaptable to resolution of ketoprofen, include the method of Doyle et al, *Pharm. Technol.* 9(2), 28–32 (1985), which utilizes conversion of the racemate to its amide derivatives for effective resolution; and that of Wainer et al, *J. Chromatogr.* 284(1), 117–124 (1984), which utilizes conversion of the drug to 1-naphthalenemethylamide derivatives.

A method for derivatizing ketoprofen, fenoprofen and other nonsteroidal anti-inflammatory drugs with optically active amphetamine (α-methylbenzeneethanamide) has been described by Singh et al, *J. Chromatogr. Biomed. Appln.* 378, 125–135 (1986). Those authors also provide a summary of the usual methods for resolving enantiomers, i.e. (1) by direct separation or chiral HPLC or GC (gas chromatographic) columns, or (2) by diastereoisomer formation, by reaction with an optically pure resolving agent, followed by chromatographic separation on an optically inactive column. Singh et al's method is a new version of the second approach, using optically active amphetamine as the resolving agent, followed by separation of the diastereoisomers by capillary gas chromatography with nitrogen-phsophorus detection. (The acid, now in optically pure form, could of course then be regenerated from the salt as is well-known.) The usual method in the art utilizes optically active α-methylbenzylamine and involves preparation of the diastereoisomeric NSAID-α-methylbenzylamide directly by means of a coupling agent (e.g. 1,1′-carbonyldiimidazole) or via the NSAID acid chloride (prepared with thionyl chloride).

More generally speaking, the S(+) isomer can be separated from racemic ketoprofen by preparing a salt of ketoprofen with an alkaloid or similar resolving agent such as cinchonidine, then separating the products by fractional crystallization from a solvent in which the dextrorotatory isomer is least soluble. The d-salt can then be acid cleaved to yield S(+) ketoprofen. Compare, for example, Alvarez U.S. Pat. No. 3,637,767, issued Jan. 25, 1972, which relates to resolution of naproxen and related compounds; and Kaiser et al, *J. Pharm. Sci.* 65(2), 269–273 (1976), which relates to resolution of ibuprofen.

While S(+) ketoprofen may be conveniently obtained by resolution of racemic ketoprofen, it may also be possible to utilize a chemical or microbiological synthetic process which will provide the S(+) enantiomer directly. One such chemical process is described in Farge et al U.S. Pat. No. 3,641,127, as already mentioned hereinabove. Another chemical process is provided by Schloemer U.S. Pat. No. 4,542,237, which describes a process for preparing α-arylalkanoic acids utilizing novel α-hydroxy alkyl aryl ketals as intermediates. As taught in column 9 of the Schloemer patent, the process is advantageous in that the α-hydroxy ketal can be resolved by well-known methods and the optically active α-hydroxy ketal thus obtained can then be used in the subject process to ultimately afford the desired acid in optically pure form.

Alternatively, a microbiological process such as that described in SHELL INTERNATIONALE RESEARCH MAATSCHAPPIJ B.V.'s European Patent Appln. No. 86 200987.5, published under No. 0 205215 on Dec. 17, 1986, may be employed. According to the European application, a pharmaceutically active compound of the type

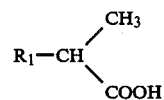

or a pharmaceutically active salt or ester thereof, which most preferably is naproxen or ibuprofen but which may be ketoprofen or various other NSAIDs, is prepared in stereospecific form by subjecting a compound of the formula

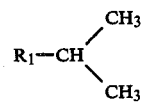

to the action of an appropriate microorganism. The desired acid is obtained having at least 70% by weight in the S-configuration. Preferably, a microorganism is selected such that the acid which is formed is at least 90% by weight in the S-configuration. Use of this method has afforded naproxen with enantiomeric distributions of 98.9% S and 1.1% R in one instance, and distributions of 99.5% S and 0.5% R in another. Processes of this type may be utilized to prepare S(+) ketoprofen for use in the present invention if the S(+) isomer can be obtained in sufficient purity [ideally, at least 90% by weight S(+) isomer.]

When S(+) ketoprofen is to be employed in the form of a pharmaceutically acceptable, analgesically active salt thereof, such salt may be conveniently prepared by direct salification of S(+) ketoprofen by known methods. See, for example, deVincentiis U.S. Pat. No. 4,440,787, which describes salts of (2′,4′-difluoro-4-biphenyl)oxypropionic acid with metallic ions, such as sodium, potassium, magnesium and calcium, or with pharmaceutically acceptable organic bases, such as lysine, arginine and diethanolamine. Compare also Armitage et al U.S. Pat. No. 4,501,727, issued Feb. 26, 1985, which describes the N-methyl-D-glucamine salt of flurbiprofen. Such a salt may not only be used in oral or rectal compositions, but, if sufficiently soluble in water, may be useful in the preparation of aqueous solutions of S(+) ketoprofen for parenteral injection.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. The method of eliciting an onset-hastened and enhanced analgesic response in a human mammal suffering from pain and in need of such treatment, comprising administering to such organism a unit dosage onset-hastening/enhancing analgesically effective amount of the S(+) ketoprofen enantiomer, and said enantiomer being substantially free of its R(−) ketoprofen antipode.

2. A method according to claim 1, wherein the weight ratio of S(+) ketoprofen to R(−) ketoprofen is greater than 9:1.

3. A method according to claim 2, wherein the weight ratio of S(+) ketoprofen to R(−) ketoprofen is greater than or approximately equal to 20:1.

4. A method according to claim 3, wherein the weight ratio of S(+) ketoprofen to R(−) ketoprofen is greater than 97:3.

5. A method according to claim 4, wherein the weight ratio of S(+) ketoprofen to R(−) ketoprofen is approximately equal to or greater than 99:1.

6. A method according to claim 1, comprising administering to such organism from about 12.5 to about 100 mg S(+) ketoprofen.

7. A method according to claim 1, comprising administering to such organism from about 12.5 to about 75 mg S(+) ketoprofen.

8. A method according to claim 1, comprising administering to such organism from about 25 to about 50 mg S(+) ketoprofen.

9. A method according to claim 2, comprising administering to such organism from about 12.5 to about 100 mg S(+) ketoprofen.

10. A method according to claim 2, comprising administering to such organism from about 12.5 to about 75 mg S(+) ketoprofen.

11. A method according to claim 2, comprising administering to such organism from about 25 to about 50 mg S(+) ketoprofen.

12. A method according to claim 3, comprising administering to such organism from about 12.5 to about 100 mg S(+) ketoprofen.

13. A method according to claim 3, comprising administering to such organism from about 12.5 to about 75 mg S(+) ketoprofen.

14. A method according to claim 3, comprising administering to such organism from about 25 to about 50 mg S(+) ketoprofen.

15. A method according to claim 4, comprising administering to such organism from about 12.5 to about 100 mg S(+) ketoprofen.

16. A method according to claim 4, comprising administering to such organism from about 12.5 to about 75 mg S(+) ketoprofen.

17. A method according to claim 4, comprising administering to such organism from about 25 to about 50 mg S(+) ketoprofen.

18. A method according to claim 5, comprising administering to such organism from about 12.5 to about 100 mg S(+) ketoprofen.

19. A method according to claim 5, comprising administering to such organism from about 12.5 to about 75 mg S(+) ketoprofen.

20. A method according to claim 5, comprising administering to such organism from about 25 to about 50 mg S(+) ketoprofen.

21. A method according to claim 1, wherein such organism is suffering from postoperative pain.

22. A method according to claim 1, wherein such organism is suffering from postpartum pain.

23. A method according to claim 1, wherein such organism is suffering from dental pain.

24. A method according to claim 1, wherein such organism is suffering from dysmenorrhea.

25. A method according to claim 1, wherein such organism is suffering from headache pain.

26. A method according to claim 1, wherein such organism is suffering from musculoskeletal pain.

27. A method according to claim 1, wherein such organism is suffering from pain or discomfort associated with a respiratory infection.

28. A method according to claim 1, wherein such organism is suffering from pain or discomfort associated with a cold or flu.

29. A method according to claim 1, wherein such organism is suffering from pain associated with inflammatory or degenerative joint disease.

30. A method according to claim 1, wherein such organism is suffering from pain associated with rheumatoid arthritis.

31. A method according to claim 1, wherein such organism is suffering from pain associated with osteoarthritis.

32. A method according to claim 1, wherein such organism is suffering from pain associated with gout.

33. A method according to claim 1, wherein such organism is suffering from pain associated with morning stiffness.

34. A method according to claim 1, wherein the S(+) ketoprofen is orally administered to such organism.

35. A method according to claim 1, wherein the S(+) ketoprofen is rectally administered to such organism.

36. A method according to claim 1, wherein the S(+) ketoprofen is topically administered to such organism.

37. A pharmaceutical composition of matter adapted to elicit an onset-hastened and enhanced analgesic response in a mammalian organism in need of such treatment, said composition comprising a solid-state unit dosage onset-hastening/enhancing analgesically effective amount of the S(+) ketoprofen enantiomer, said enantiomer being substantially free of its R(−) antipode, and a nontoxic pharmaceutically acceptable carrier or diluent therefor.

38. The pharmaceutical composition of matter according to claim 37, adapted for oral administration.

39. The pharmaceutical composition of matter according to claim 38, formulated as a tablet, caplet, pill or capsule.

40. The pharmaceutical composition of matter according to claim 37, adapted for rectal administration.

41. The pharmaceutical composition of matter according to claim 40, formulated as a suppository.

* * * * *